US006991736B2

(12) United States Patent
Downs (10) Patent No.: US 6,991,736 B2
(45) Date of Patent: Jan. 31, 2006

(54) STRUCTURE AND PROCESS FOR CONTINUOUSLY TREATING DENTAL UNIT WATER

(76) Inventor: Bradley J. Downs, 18885 Pebble Beach Way, Monument, CO (US) 80132

( * ) Notice: Subject to any disclaimer, the term of this patent is extended or adjusted under 35 U.S.C. 154(b) by 113 days.

(21) Appl. No.: 10/474,642

(22) PCT Filed: Apr. 9, 2002

(86) PCT No.: PCT/US02/10969

§ 371 (c)(1),
(2), (4) Date: Oct. 9, 2003

(87) PCT Pub. No.: WO02/081378

PCT Pub. Date: Oct. 17, 2002

(65) Prior Publication Data

US 2004/0108271 A1 Jun. 10, 2004

Related U.S. Application Data

(60) Provisional application No. 60/282,376, filed on Apr. 9, 2001.

(51) Int. Cl.
C02F 1/68 (2006.01)

(52) U.S. Cl. .................. 210/764; 210/668; 210/669; 210/748; 422/105; 204/229

(58) Field of Classification Search ............ 210/764, 210/668, 669, 748; 422/105; 204/229
See application file for complete search history.

(56) References Cited

U.S. PATENT DOCUMENTS

| 5,147,203 | A | | 9/1992 | Seidenberg |
| 5,158,454 | A | | 10/1992 | Viebahn et al. |
| 5,217,626 | A | * | 6/1993 | Yahya et al. ............. 210/764 |
| 5,230,624 | A | | 7/1993 | Wolf et al. |
| 5,318,443 | A | | 6/1994 | Overmyer |
| 5,401,399 | A | | 3/1995 | Magnusson et al. |
| 5,526,841 | A | | 6/1996 | Detsch et al. |
| 5,709,545 | A | | 1/1998 | Johnston et al. |
| 5,709,546 | A | | 1/1998 | Waggoner |
| 5,837,204 | A | * | 11/1998 | Prevost et al. ............. 422/105 |
| 5,942,125 | A | | 8/1999 | Engelhard et al. |
| 5,961,326 | A | | 10/1999 | Johnston et al. |
| 6,019,117 | A | | 2/2000 | Detsch et al. |
| 6,106,771 | A | | 8/2000 | Fitton |
| 6,142,170 | A | | 11/2000 | Belfer et al. |
| 6,159,007 | A | | 12/2000 | Sorensen |

(Continued)

OTHER PUBLICATIONS

Shannon E. Mills, DDS, "The Dental Unit Waterline Controversy: Defusing the Myths, Defining the Solutions", The Journal of the American Dental Association, Oct. 2000, vol. 131, pp. 1427-1441.

(Continued)

*Primary Examiner*—W. L. Walker
*Assistant Examiner*—Krishnan S. Menon
(74) *Attorney, Agent, or Firm*—Townsend and Townsend and Crew LLP (57) ABSTRACT

The invention pertains generally to dental units (e.g., a high-speed dental handpiece (11), an ultrasonic scaler (13) and an air/water syringe (12)) connected to a water supply that provides coolant and rinse water to the dental units. More particularly the invention pertains to a dental unit using water that is continuously treated with a water treatment agent, such as microbiocidal silver ions. The treated dental unit water is supplied to the dental units via dental unit waterlines (6, 7, 8, 9, and 10).

7 Claims, 4 Drawing Sheets

U.S. PATENT DOCUMENTS

| | | |
|---|---|---|
| 6,212,333 B1 | 4/2001 | Olk et al. |
| 6,250,920 B1 | 6/2001 | Overmyer |
| 6,267,895 B1 | 7/2001 | Engelhard et al. |
| 6,325,944 B1 * | 12/2001 | DeSanto ............... 210/748 |
| 6,464,868 B1 | 10/2002 | Korin |
| 6,482,370 B2 | 11/2002 | Holsclaw et al. |
| 6,514,413 B2 * | 2/2003 | Pimenov et al. ............ 210/668 |
| 6,544,427 B2 | 4/2003 | Layton |
| 6,555,055 B1 | 4/2003 | Cisar et al. |
| 6,619,302 B2 | 9/2003 | Labib et al. |
| 2001/0009239 A1 * | 7/2001 | Shiau et al. ............ 210/764 |
| 2001/0052487 A1 * | 12/2001 | King .................. 210/169 |
| 2003/0178374 A1 * | 9/2003 | Arata .................. 210/758 |

OTHER PUBLICATIONS

Evaluation of Antimicrobial Potential of BioRX™, Final Report, Research Services, Center for Dental Research, Loma Linda University School of Dentistry, Loma Linde CA, Loma Linda CA, Mar. 30, 2001.

Effect of BioRx Solutions on Enamel Bond Strength, Final Report, Center for Dental Research, Loma Linda University School of Dentistry, Loma Linda, CA, Apr. 20, 2001.

* cited by examiner

STRUCTURE AND PROCESS FOR CONTINUOUSLY TREATING DENTAL UNIT WATER

CROSS-REFERENCE TO RELATED APPLICATIONS

This application claims the benefit of U.S. Provisional Application 60/282,376, filed Apr. 9, 2001, the entire contents of which are hereby incorporated by reference.

BACKGROUND OF THE INVENTION

Microorganisms colonize dental units and contaminate dental treatment water. The formation of biofilm on water-bearing surfaces in dental units results in fouling of the water that passes through the unit with high levels of suspended bacteria. In 1993 the Centers for Disease Control and Prevention (CDC) recommended infection control practices for dentistry. The recommendations included flushing waterlines daily for several minutes and for 20 to 30 seconds between patients. The 1996 American Dental Association (ADA) statement on dental unit waterlines (DUWL) challenged the dental manufacturing industry to develop methods to control biofilm in dental unit water systems. The statement established a goal for dental water to contain no more than 200 CFU/ml (colony forming units per milliliter) of heterotrophic bacteria. The Organization for Safety and Asepsis Procedures (OSAP) issued a statement in 1996 supporting both the CDC and ADA guidelines, but containing more explicit guidance on waterline monitoring and the use of sterile irrigants in surgery. It was reported in the Journal of American Dental Association (JADA) in October of 2000 that heterotrophic bacteria counts ranging between 10,000 and 100,000 CFU/ml may be commonplace. The Safe Drinking Water Act establishes a 500 CFU/ml standard for non-coliform bacteria in drinking water.

Current approaches to improve the quality of dental water include waterline flushing, independent reservoirs filled with distilled water, chemical "shock treatment," continuous chemical treatment, mechanical filtration and automated in-line treatment devices. Waterline flushing may temporarily reduce bacteria levels, however the biofilm remains completely active, and at any given time a patient may be exposed to elevated levels of bacteria. Independent water reservoirs filled with distilled water may begin free of bacteria, however without a residual disinfectant the water is readily contaminated from the biofilm within the DUWL.

Mechanical filtration may be temporarily effective at filtering bacteria, however problems with breakthrough, time and costs of replacement are prohibitive. In dentistry, "shock treatments" utilizing solutions with bleach, peroxide, or chlorhexidine have been administered, but the "shock treatments" must be repeated (e.g., every day) because the biofilm begins to regrow in that period of time. This type of system also requires use of only sterile water to slow down the biofilm formation. Mature biofilms are notoriously resistant to chemical disinfection including these "shock treatments." Thus, if a practitioner does not treat his system for several weeks, the biofilm will become resistant to this method. Most biocidal agents have not been shown to destroy a mature biofilm.

U.S. Pat. No. 5,158,454 to Viebahn, incorporates an automated in-line ozone generator that is effective at continuous disinfection. This device and others similar to it are bulky, taking up limited space from the operatory unit and are expensive to install and operate.

Another system desired to control the presence of infectious microbes in water supplied to dental units is disclosed in U.S. Pat. No. 5,230,624 to Wolf et al. Here, an in-line filter is provided in a supply line leading to a dental instrument, such as a drill or the like, and contains a polyiodide purification resin. The resin functions to neutralize and kill bacteria by the release of iodine from the resin surface to the bacteria through a demand release process involving electrostatic attraction. The resin is positively charged such that the negatively charged microorganisms are attracted to the resin to the point where iodine is released directly into the microorganism. The use of iodine to treat the water may cause the water to have a foul odor and/or taste.

Another system for controlling the presence of infectious microbes in water supplied to dental units is disclosed in U.S. Pat. No. 5,709,546 to Waggoner. The system disclosed in U.S. Pat. No. 5,709,546 provides a process by which mature biofilms, including biofilms of the type produced by gram negative bacteria such as *Pseudomonas aeruginosa*, are reduced to the point of elimination through the use of a hydroxycarboxylic acid in relatively low concentrations so as not to be harmful to human tissue. This invention requires strict metering control of the acid and any malfunctions can result in harmful conditions to human tissue.

Therefore, a need exists for a dental water treatment agent that is bactericidal but not toxic or irritating to humans. The treated water should not have an unpleasant taste or odor. The system should detach biofilm and discourage subsequent reformation, while protecting the dental unit's internal components from corrosion or degradation. If delivered continuously in treatment water, the system should not have any effect on enamel or dentin bonding agents.

BRIEF SUMMARY OF THE INVENTION

The present invention pertains to methods for purifying dental water from heterotrophic bacteria. These methods involve the administration of a microbiocidally or bacteriostatically effective amount of metal ions and/or metal ion salt(s) to the source water. The administration of these metal ions and/or metal ion salt(s) to the source water causes microorganisms that are present to be killed or maintained in a non-growth status.

The present invention also pertains to delivery systems for use in treating the source dental water with metal ions and/or metal ion salts. These delivery systems are solid or liquid formulations or mechanical devices that release metal ions and/or metal ion salt(s) to the source dental water.

Advantages of the present invention include the manner of source dental water treatment and efficacy of consistently and continuously reducing bacteria levels. With the present invention, water continuously treated with metal ions and/or metal ion salts will be non-toxic, non-irritating, non-corrosive, will not affect enamel or dentin bonding agents, and it does not have in excess of 200 CFU/ml of heterotrophic bacteria. Continuous disinfection of a DUWL will prevent additional biofilm growth and eventually dead bacteria will slough and the biofilm formation will be reversed.

Aspects of the invention include a method of continuously treating dental unit water. The method administers a metal water treatment agent into source water to initiate residual disinfection properties into the source water in order to change the source water to treated dental unit water. The treated dental unit water is supplied to at least one dental instrument via at least one dental unit waterline.

Preferably, the metal water treatment agent comprises at least one metal ion and/or at least one metal ion salt. The metal ion and/or metal ion salt is preferably silver, but may be zinc, gold or copper. More preferably, the metal ion salt or compound comprises one or more of the following: colloidal silver, silver carbonate, silver chlorate, silver perchlorate, silver phosphate, silver bromate, silver iodate, silver periodate, silver nitrate, silver nitrite, silver citrate, silver thiosulfate, silver oxide, silver peroxide, silver sulfide, silver fluoride, silver chloride, silver bromide, silver iodide, silver carboxylates, silver protein. Preferable are colloidal silver, silver oxide, silver phosphate, silver carbonate, silver iodate, silver citrate or silver chloride.

The treated dental unit water is non-toxic and non-irritating to humans. The treated dental unit water is non-corrosive to the dental unit waterline. The treated dental unit water does not affect enamel or dentin bonding agents. The treated dental unit water may result in continuous disinfection of the source water which prevents additional biofilm growth and/or causes dead bacteria to slough and biofilm formation to be reversed. The treated dental unit water reduces chances of periodontal disease formation.

Administering the water treatment agent may comprise generating metal ions into the dental unit water from the water reservoir by passing the source water through a metal ion generator having a negative electrode and a positive metal electrode by which the negative charge from the negative electrode draws positive metal ions from the positive electrode into the treated dental unit water.

The source water may be directly plumbed into the dental unit water line and the metal ion generator may be installed at each dental unit waterline. Alternatively, the administering the water treatment agent may occur at a point of entry prior to entry into at least one lateral waterline.

The source water is from an independent water purifier. The independent water purifier may a reverse osmosis technology or a distillation technology.

A concentration of metal ions and/or metal salts may be provided in an aqueous environment in a quantity so as to cause disinfection of existing live bacteria established in the dental unit waterline and/or to cause bacteriostatic conditions in the dental unit waterline.

Metal ions may be added into water by passing the source water through water-permeable element having received therein a metal ion sustained release source. The metal ion sustained release source may be an amorphous soluble glass, a zeolite resin, or a styrene resin containing metal ions.

The source water may be directly plumbed into the dental unit waterline and the metal ion sustained release source may be installed at each dental unit waterline. Administering the water treatment agent may occur at a point of entry prior to entry into at least one lateral waterline and the source water may be treated with the metal ion sustained release source and subsequently routed to each dental unit waterline.

The water treatment agent may comprise stabilized metal ions. The water treatment agent may comprise a metal sodium chloride ion salt formed by stabilizing the metal ions in sodium chloride. The metal sodium chloride ion salt may be delivered in a hydrated liquid, in an anhydrous form, or in an anhydrous metal sodium chloride tablet.

The metal sodium chloride ion salt may be administered to an independent reservoir.

Other aspects of the invention include a device for continuously treating dental water. The device comprises a housing having a first open end configured to permit source water to enter the housing. A water treating media comprising a water treatment agent is encased within the housing and configured to release the water treatment agent into the source water to transform the source water into treated dental water. A filter is disposed within the first open end and configured to keep the media encased within the housing and to release the treated dental water into a dental unit water line.

The water treating media may be a resin.

The water treatment agent may be a bactericide which preferably comprises a metal ion. The bactericide may comprise a metal ion salt or compound. Alternatively, the water treatment agent may include a flavor, a colorant and/or an odorant in addition to or instead of the bactericide.

BRIEF DESCRIPTION OF THE DRAWINGS

These, as well as other features of the present invention, will become apparent upon reference to the drawings, wherein.

DETAILED DESCRIPTION OF THE INVENTION

The present invention proceeds in a manner contrary to the prior art procedures discussed above relating to shock treatment or mechanical filtration. The invention utilizes continuous chemical treatment including batch treatment of source water placed in independent reservoirs and continuous treatment of a pressurized source. The present invention enables the use of antimicrobial metal ions in low concentrations that are consistent with water to be used in dental or drinking water applications.

Preferably, the metal ions are silver ions, salts, or compounds. Examples of silver ion salts or compounds include, colloidal silver, silver carbonate, silver chlorate, silver perchlorate, silver phosphate, silver bromate, silver iodate, silver periodate, silver nitrate, silver nitrite, silver citrate, silver thiosulfate, silver oxide, silver peroxide, silver sulfide, silver fluoride, silver chloride, silver bromide, silver iodide, silver carboxylates, silver protein. Preferable are colloidal silver, silver oxide, silver phosphate, silver carbonate, silver iodate, silver citrate and silver chloride. It will be appreciated that other silver ions or ion salts may be used. It will also be appreciated that other metals, such as zinc, gold or copper may be used. The metal ion salts or compounds are at a low concentration that is not likely to cause damage to soft tissue or otherwise be harmful to a patient. Water continuously treated with metal ions and/or metal ion salts, or metal ion compounds preferable silver ions, will be non-toxic, non-irritating, non-corrosive, and will not affect enamel or dentin bonding agents. The treated water will not have in excess of 200 CFU/ml of heterotrophic bacteria.

The present invention attacks not only the water-born bacteria but also, more importantly, the biofilm bacteria. By eliminating the mature biofilm through a constant supply of an effective potable biocide, this major source of contamination is eliminated. Continuous disinfection of a DUWL will prevent additional biofilm growth and eventually dead bacteria will slough and the biofilm formation will be reversed. The chances of periodontal disease formation are also reduced.

An independent third party reputable dental university that concluded the efficacy of this invention has conducted several studies. A flow-through metal ion generator was used to prepare ten gallons of distilled water with an ionized silver concentration of 2.8 to 4 parts per milliliter (ppm). In the study, the results of which are shown in Table I, ten operatory units were treated with the prepared silver ionized water for a period of two weeks. Initial concentrations of heterotrophic bacteria ranged from 120 to 12,580 CFU/ml. In all ten operatory units, bacteria levels were reduced to zero in no more than one week.

TABLE I

| | Heterotrophic CFU/ml | | | |
|---|---|---|---|---|
| Unit No. | Baseline | 1 Day | 3 Days | 11 Days |
| 1 | 180 | 0 | 0 | 0 |
| 2 | 2,020 | 0 | 0 | 0 |
| 3 | 12,580 | 0 | 0 | 0 |
| 4 | 10,000 | 20 | 40 | 0 |
| 5 | 160 | 20 | 20 | 0 |
| 6 | 7,760 | 0 | 0 | 0 |
| 7 | 160 | 0 | 0 | 0 |
| 8 | 10,000 | 40 | 0 | 0 |
| 9 | 120 | 0 | 0 | 0 |
| 10 | 10,000 | 0 | 0 | 0 |

A flow-through metal ion generator is referenced herewith for the purpose of treating continuous flow source water originating from a municipal source. The flow-through metal ion generator generates metal ions into water by passing the water through an instrument that comprises a negative electrode and a positive metal electrode by which the negative charge from the negative electrode draws positive metal ions from the positive electrode into the water. The municipal water may be pretreated to remove impurities by means of distillation, reverse osmosis, de-ionization, ultraviolet disinfection, or other technologies.

Metal ion salts are administered to water reservoir systems by means of adding the metal ion salt in liquid or solid form. The preferred metal ion salt is silver sodium chloride. Concentrated solutions of ionized silver (colloidal metal) are highly light sensitive and become oxidized forming a gray to black silver oxide precipitate. Colloidal silver in concentrations generally above 10 ppm will turn yellow and become brown at even higher concentrations. A stabilized silver halide solution, preferably silver sodium chloride will remain clear to white in color at concentrations exceeding 100 ppm. The silver sodium chloride solution can be prepared into an anhydrous state by evaporating off the water. The silver sodium chloride powder can be further processed into pressed tablets. In exemplary embodiments, the concentration of metal ion in an aqueous environment is in the range of 1 ppm to 10 ppm so as to cause disinfection of existing live bacteria established in the DUWL. In other embodiments, the concentration of metal ion in an aqueous environment is preferably in the range of 0.02 ppm to 1 ppm so as to cause bacteriostatic conditions in the dental unit.

Exemplary embodiments of the present invention provide for continuous disinfection of water added to a dental unit reservoir by administering the metal ion salt into the reservoir in the liquid, powder, or tablet form. The water may be from any of the previously described sources. The efficacy of this invention was confirmed in a second study conducted by an independent third party dental university. The results of the study are shown in Table II. Four operatory units with existing reservoir systems were provided with the prepared silver sodium chloride product for a period of six weeks. In this study, the concentration of ionized silver was reduced to a range of 0.02 to 0.05 ppm to evaluate the bacteriostatic efficacy. The operatory units were initially shock treated with an organic acid and subsequent peroxide/silver solution to reduce the baseline heterotrophic bacteria levels. Throughout the entire six-week study, heterotrophic bacteria levels for all four operatory units remained below 3 CFU/ml.

TABLE II

| Operatory Unit | Heterotrophic CFU/ml | | | | | | |
|---|---|---|---|---|---|---|---|
| | Baseline | Week 1 1/26 | Week 2 2/2 | Week 3 2/9 | Week 4 2/16 | Week 5 2/23 | Week 6 3/5 |
| 1 | 1200 | 0 | 20 (1) | 3 | 0 | 1 | 0 |
| 2 | 4,740 | 0 | 0 | 0 | 0 | 0 | 0 |
| 3 | 40 | 0 | 0 | 0 | 1 | 1 | 0 |
| 4 | 3,620 | 0 | 0 | 0 | 2 | 0 | 0 |

(1) No silver product was detected in sample

Preferably, metal ions are continuously delivered by means of a flow through metal ion impregnated resin media. Metal ions are administered by passing source water through a water-permeable container or element having received therein a metal ion sustained release source. The metal ion sustained release source may be for example an amorphous soluble glass, a zeolite resin or styrene resin (e.g., an acrylic divinylbenzene structure with carboxylic exchange groups) containing metal ion(s). The amount of metal ion sustained release source required is dependent on the desired effective life span and flow rate of water. The metal ion sustained release source may be installed at the dental operatory unit plumbed directly into a municipal water source or it may be installed in the reservoir drop tube allowing for continuous treatment of batch water placed into the reservoir. A larger metal ion sustained release source may be installed at the building water source point-of-entry or within a water purification system.

A major concern with the administration of continuous chemical treatment is the potential negative effect on enamel or dentin bonding agents. An independent third party reputable dental university conducted an additional study to substantiate the effect of silver sodium chloride on enamel or dentin bonding agents. Results of the study concluded that the treatment of human enamel surface with silver sodium chloride solution up to 200 ppm does not adversely affect the bond strength.

Figure 1:
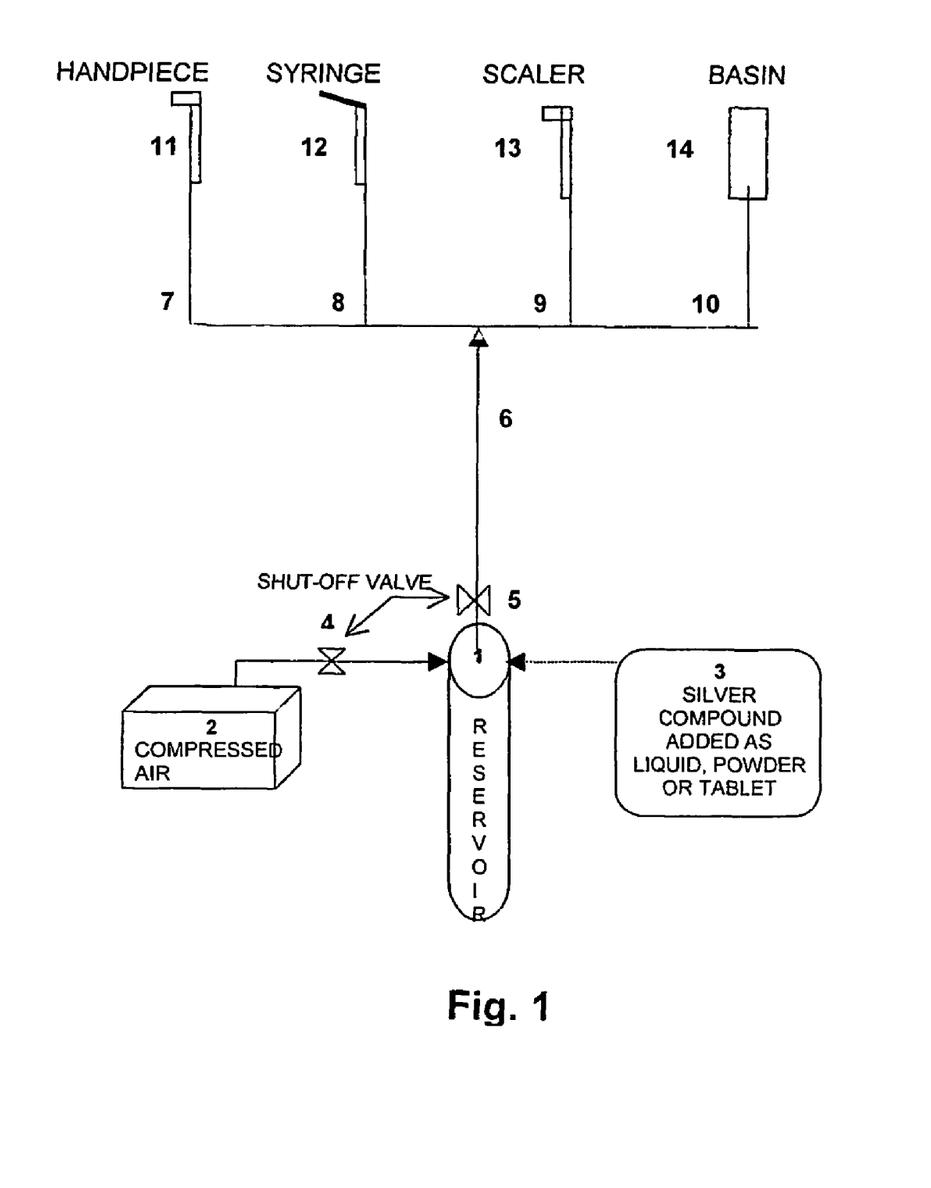
FIG. 1 is an overall diagram of a first embodiment of the present invention wherein treatment of dental water is administered manually in a batch mode in a system having a typical dental unit wherein the water source is a water bottle or reservoir.

Referring now to the drawings wherein the showings are for purposes of illustrating preferred embodiments of the present invention only, and not for purposes of limiting the same, FIG. 1 illustrates a first embodiment where the components of the water disinfecting system are integrated with a typical dental unit. From the water reservoir 1, a water treatment agent is administered to initiate residual disinfection properties in the water. The water treatment agent is a metal ion or metal ion salt, preferably, silver ion salt. Compressed air 2 is allowed to pressurize the reservoir 1 by placing the valve 4 in the open position. Pressurized water containing residual disinfectant in reservoir 1 is allowed to fill dental unit water lines 6, 7, 8, 9 and 10 that supply instruments 11, 12, 13 and 14, respectively, by placing valve 5 in the open position.

Figure 2:
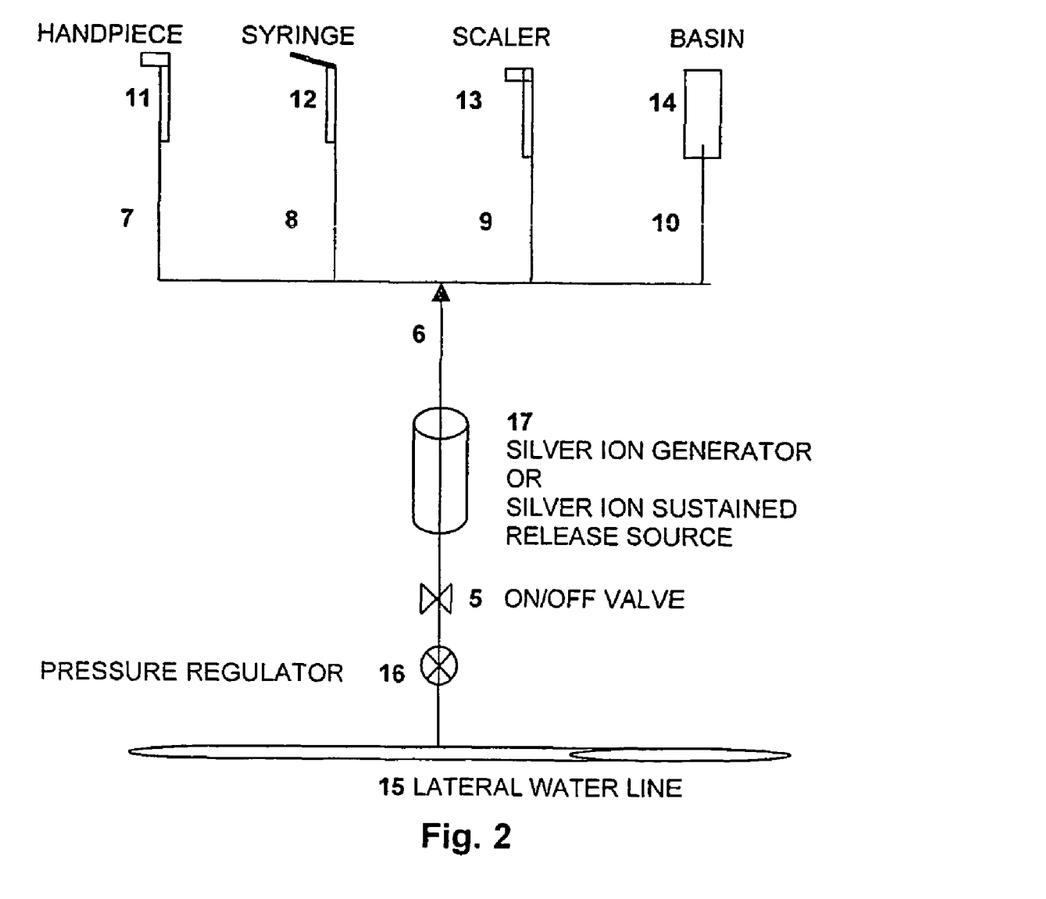
FIG. 2 is an overall diagram of a second embodiment of the present invention wherein treatment of dental water is incorporated into each dental unit, commonly referred to as point-of-use (POU) treatment, and wherein the water source is a lateral line from a pressurized water main or water treatment system.

FIG. 2 illustrates a second embodiment of the present invention similar to the embodiment shown in FIG. 1 wherein the water source is a lateral line 15 from a pressurized water main or water treatment system. The water treatment is incorporated into each dental unit, commonly referred to as point-of-use (POU) treatment.

Figure 3:
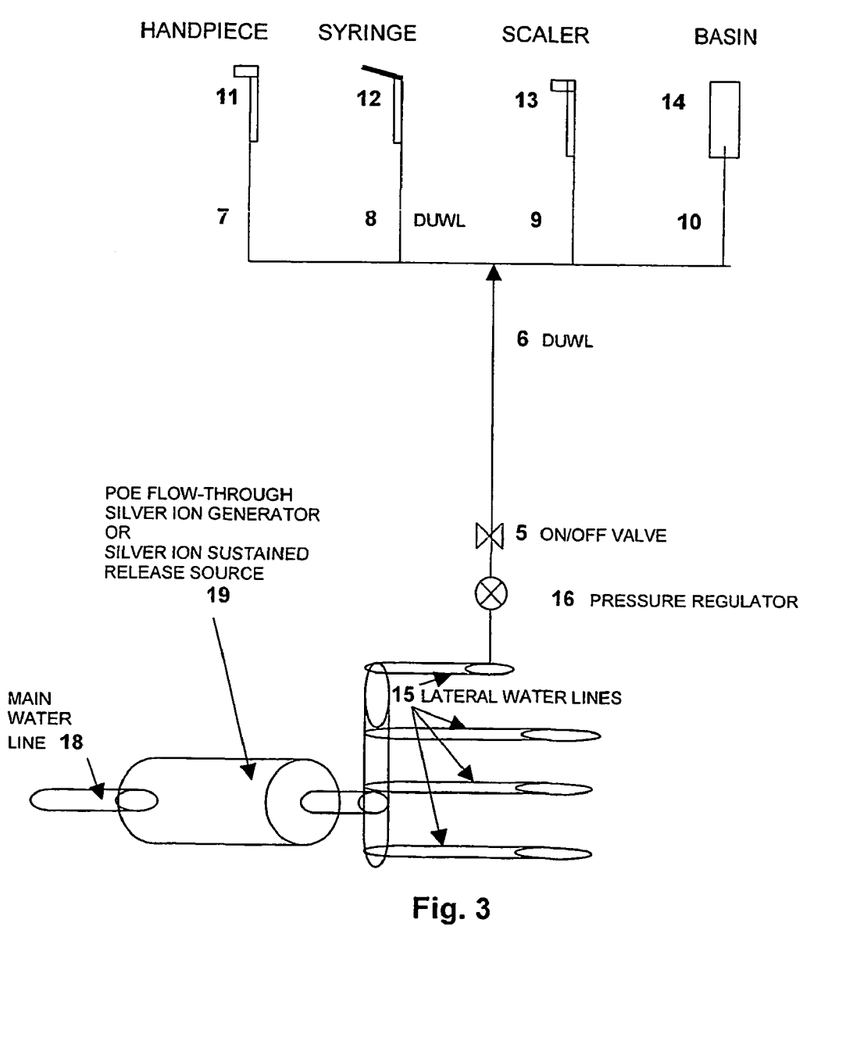
FIG. 3 is an overall diagram of a third embodiment of the present invention wherein treatment of the dental water is incorporated into the main water line, commonly referred to as point-of-entry (POE) treatment, and wherein the water source is a lateral line from a pressurized water main or water treatment system

FIG. 3 illustrates a third embodiment of the present invention similar to the embodiments shown in FIGS. 1 and 2 wherein the water source is a lateral line 15 from a pressurized water main 18 or water treatment system 18 and the water treatment is incorporated into the main water line 18, commonly referred to as point-of-entry (POE) treatment.

Figure 4:
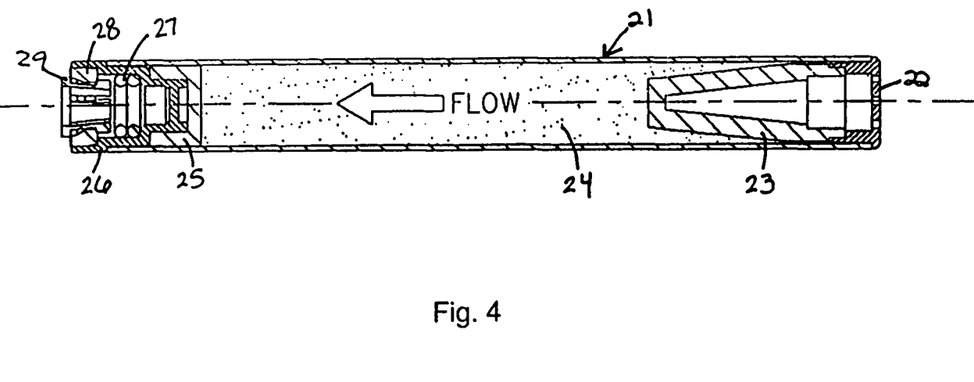
FIG. 4 illustrates a fourth embodiment of the present invention wherein treatment of dental water is administered continuously through a "pickup tube" in a system having a typical dental unit wherein the water source is a water bottle or reservoir.

FIG. 4 illustrates a fourth embodiment of the present invention wherein treatment of dental water is administered continuously through a "pickup tube" 21 in a system having a typical dental unit wherein the water source is a water bottle or reservoir. Dental water flows up through a screen 22 connected to a filter membrane 23, through media 24, all contained within the housing 21 and filter membranes 23, 25. In exemplary embodiments, the media 24 includes a metal ion sustained release source and an activator. The activator provides preferential ions which increase ion exchange for facilitating a release of a higher level of metal ions into the treated dental unit water. In exemplary embodiments, the activator is citric acid. In other embodiments, the media may include a colorant, flavor and/or an odorant in addition to or instead of the metal ion sustained release source. For example, a blue colorant may be used in conjunction with the metal ion sustained release source. Thus, if the dental water has a blue tint, the dental practitioner can easily tell that the water is treated dental water. The housing connector 26 allows for a tube connection, which is preferably ¼-inch, with the cartridge consisting of an o-ring(s) 27, body insert 28, and collect 29.

Figure 5:
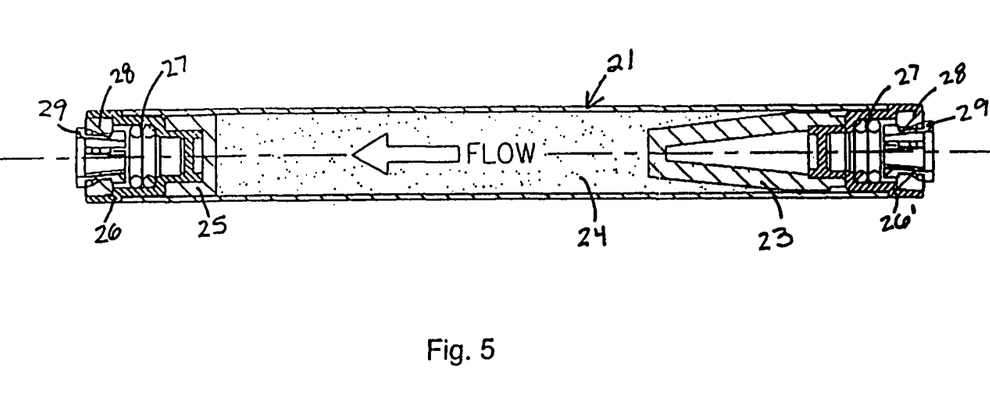
FIG. 5 illustrates a fifth embodiment of the present invention wherein treatment of the dental water is administered continuously by means of an inline housing mechanism wherein the water source is a lateral line from a pressurized water main or water treatment system.

FIG. 5 illustrates a fifth embodiment of the present invention wherein treatment of the dental water is administered continuously by means of an inline housing mechanism wherein the water source is a lateral line from a pressurized water main or water treatment system. Dental water flows through a housing connector 26' that allows for a tube connection, which is preferably ¼-inch, with a cartridge consisting of an o-ring(s) 27, body insert 28, and collect 29. The housing connector 26' is joined to a filter membrane 23. Dental water flows through the filter membrane 23, through media 24 consisting of metal ion sustained release source, activator, and possibly colorant, all of which are contained within the housing 21 and filter membranes 23, 25. The downstream housing connector 26 allows for a ¼ inch tube connection with the cartridge embodiment consisting of an o-ring(s) 27, body insert 28, and collect 29.

While the invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. A method of continuously treating dental unit water, comprising:
   passing the source water through a water-permeable element having received therein a metal ion sustained release source that releases into the source water at least one microbiocidal metal ion selected from the group consisting of silver, zinc, gold and copper ions to initiate residual disinfection properties into the source water, thereby changing the source water to a treated dental unit water;
   wherein the metal ion release source comprises a colorant, flavorant and/or odorant that is released into the treated dental water to provide an indication as to when the metal ions are initially present in the treated dental water, and
   supplying the treated dental unit water to at least one dental instrument via at least one dental unit waterline whereby the residual disinfection properties of the treated dental unit water are sufficient to kill existing biofilm established in the dental unit and reduce additional biofilm growth.

2. The method of claim 1, wherein the metal ion release source comprises an activator configured to provide preferential ions which increase ion exchange for facilitating a release of a higher level of metal ions into the treated dental unit water.

3. A method of eliminating biofilm in a dental unit which comprises:
   mixing a disinfectant consisting essentially of silver nitrate or silver citrate in powder or tablet form with source water, thereby releasing microbiocidally effective amounts of silver ions into source water to provide residual disinfection properties in the source water, thereby changing the source water to a treated dental unit water; and
   supplying the treated dental unit water to at least one dental instrument via at least one dental unit waterline, whereby the residual disinfection properties of the treated dental unit water are sufficient to kill existing biofilm established in the dental unit and reduce additional biofilm growth therein.

4. The method of claim 3 wherein the concentration of silver ions in the treated dental unit water is less than 200 ppm.

5. The method of claim 4 wherein the concentration of silver ions in the treated dental unit water is in the range of 1 ppm to 50 ppm so as to cause disinfection of live bacteria established in the dental unit.

6. The method of claim 4 wherein the concentration of silver ions in the treated dental unit water is in the range of 0.02 ppm to 1.0 ppm so as to maintain residual bacteriostatic conditions in the dental unit.

7. A method of maintaining clean dental units, including dental unit water lines and dental instruments, which method comprises:

admixing, in an independent water reservoir, source water and at least one tablet consisting essentially of silver nitrate or silver citrate to provide a concentration of silver ions sufficient to impart residual disinfection properties to the source water without having a negative effect on dental enamel or dentin bonding agents; thereby changing the source water to treated dental water; and supplying the treated dental unit water to at least one dental instrument via at least one dental unit waterline, whereby the residual disinfection properties of the treated dental unit water are sufficient to kill existing biofilm established in the dental unit and reduce additional biofilm growth therein.

* * * * *